United States Patent [19]
Cho

[11] Patent Number: 4,803,715
[45] Date of Patent: Feb. 7, 1989

[54] THICKNESS MEASUREMENT WITH AUTOMATIC CORRECTION FOR CHANGES IN COMPOSITION

[75] Inventor: Boong Y. Cho, Columbus, Ohio

[73] Assignee: Process Automation Business, Inc., Columbus, Ohio

[21] Appl. No.: 918,162

[22] Filed: Oct. 10, 1986

[51] Int. Cl.$^4$ .............................................. G01B 15/02
[52] U.S. Cl. ........................................ 378/90; 378/89
[58] Field of Search ................... 378/51, 54, 56, 89, 378/90

[56] References Cited

U.S. PATENT DOCUMENTS

| | | | |
|---|---|---|---|
| 3,046,402 | 7/1962 | Cherry | 378/54 |
| 3,766,383 | 10/1973 | Harris et al. | 378/51 |
| 4,007,373 | 2/1977 | Torguet et al. | 378/51 |
| 4,047,029 | 9/1977 | Allport | 378/90 |
| 4,088,886 | 5/1978 | Moulton | 378/46 |
| 4,182,954 | 1/1980 | Giles | 250/308 |
| 4,228,351 | 10/1980 | Snow et al. | 378/54 |

FOREIGN PATENT DOCUMENTS 1384245 2/1975 United Kingdom ................ 378/54

Primary Examiner—Craig E. Church
Assistant Examiner—John C. Freeman
Attorney, Agent, or Firm—Richard H. Berneike

[57] ABSTRACT

An apparatus for measuring the thickness of a sheet of metal by irradiating the sheet with x-rays. The intensity of the initial x-rays, the transmitted x-rays, and the backscattered x-rays are detected and the detector signals are processed to produce a signal representing the thickness of the metal sheet.

9 Claims, 1 Drawing Sheet

THICKNESS MEASUREMENT WITH AUTOMATIC CORRECTION FOR CHANGES IN COMPOSITION

BACKGROUND OF THE INVENTION a. Field of the Invention

This invention relates to measuring the thickness of a sheet of metal alloy during its production. More particularly, the invention relates to a thickness measurement system which directs X-radiation toward the sheet, detects both the intensity of radiation transmitted therethrough and the intensity of radiation backscattered therefrom, and produces electrical signals expressive of said intensities that, when appropriately processed, yield a measurement of sheet thickness that accounts for small changes in composition of the sheet.

b. Background Art

Systems for determining the thickness of metal sheet via non-contacting radiation gauging techniques are well known. Such systems typically employ some form of the Bouguer Law:

$$I = I_0 e^{-mdt} \quad (1)$$

where "$I_0$" is the intensity of radiation incident upon the sheet, "$I$" is the intensity of radiation transmitted through the sheet, "$m$" is the mass attenuation coefficient of the sheet, and "$d$" and "$t$" are the density and thickness, respectively, of the sheet. Equation 1 may be expressed as follows:

$$-\ln(I/I_0) = m(dt) \quad (2)$$

This relation approximately holds where the composition of the sheet is uniform and relatively constant. To make the relationship more precise, "$m$" is typically expressed as a polynomial function of the logarithm of transmittance ($I/I_0$). This is necessitated by the fact that the value of "$m$" will change with thickness. Accordingly, the system is typically calibrated by measuring the transmittance for several samples of known composition but varying thickness, and using the measurements to derive values for the polynomial function. If the sheet to be measured has a composition that is known and uniform, the value of "$d$" is known and the transmittance of the sheet can be measured to produce, by appropriate manipulation of Equation 2, a measurement of the sheet thickness.

The measurement problem is more complicated when the sheet is an alloy and the alloy composition varies. Although the variation is typically very small, a small variation in composition can have a pronouncedly adverse effect on the thickness measurement.

U.S. Pat. No. 4,047,029 Allport discloses a self-compensating X-ray thickness gauge that uses a combination of transmission and scattering measurements to compute thickness. Thickness is computed via an intermediate step of computing a mass attenuation coefficient that is corrected for deviations from the composition of a standard reference alloy. The calibration process requires two sets of samples (standards), and the described measurement system embodies an assumption that changes in density resulting from deviations in composition can be ignored.

SUMMARY OF THE INVENTION

This invention provides apparatus and associated methods for measuring the thickness of a sheet of metal alloy, which apparatus are calibrated with samples of a reference alloy, and which sheet has a composition that may vary from the reference alloy, wherein the sheet is irradiated by a source of X-rays and the intensities of X-rays which are emitted from the source, transmitted through the sheet, and backscattered from the sheet are separately measured to produce reference, transmission, and scattering signals, respectively, and wherein signal processing means are employed to produce a thickness response that is derived from said signals, characterized in that the signal processing means employs the reference and scattering signals to produce a second ratio response, employs the reference and transmission signals to produce a comparison response that indicates what the second ratio response should be if the composition of the sheet is equal to the reference alloy, and produces a thickness response expressive of the thickness of the sheet, the magnitude of which thickness response depends upon the degree to which the second ratio response differs from the comparison response.

The thickness response may be produced by prior computation of the basis weight and density of the sheet, as corrected for composition variations from the reference alloy.

DETAILED DESCRIPTION

Figure 1:
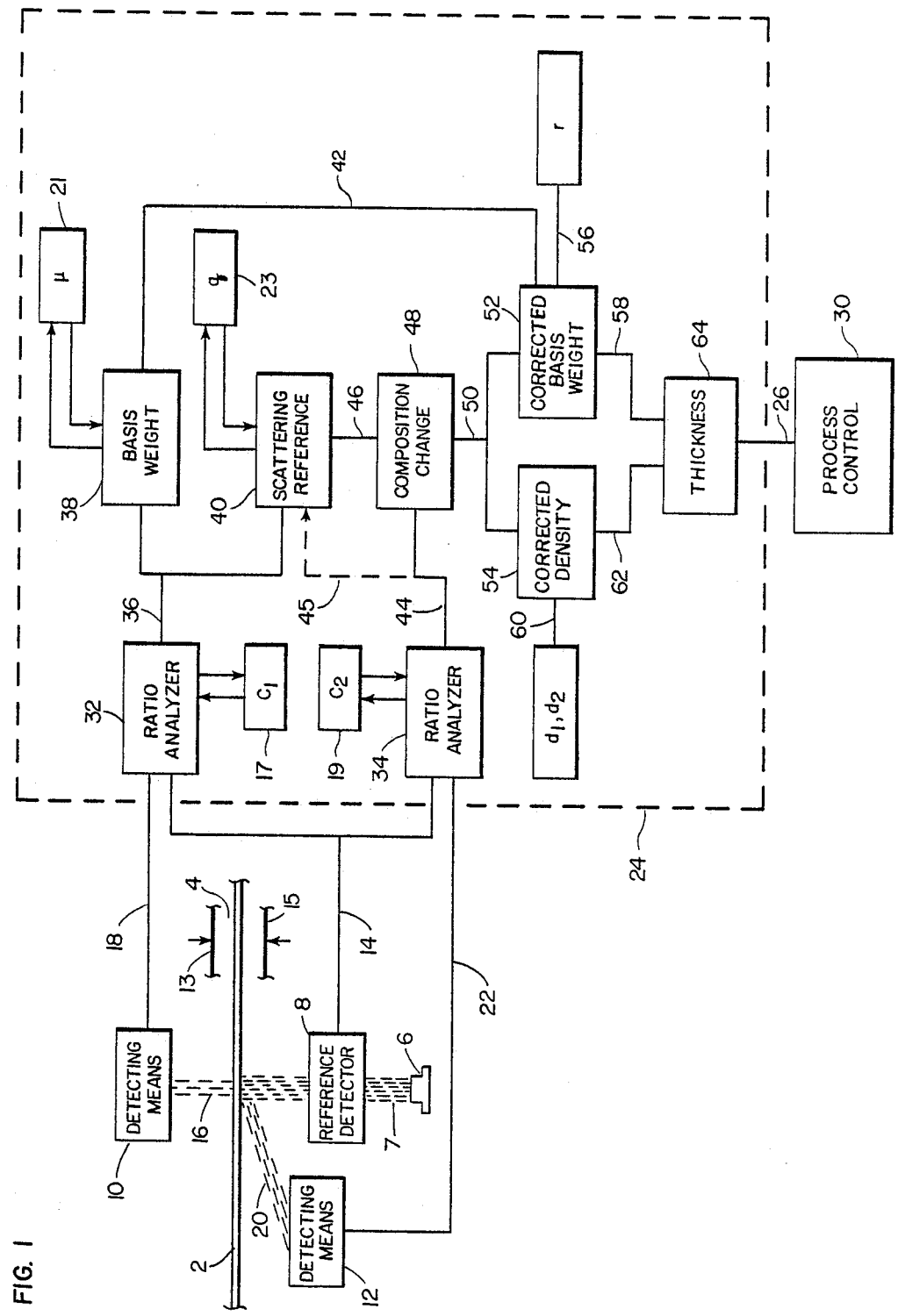
FIG. 1 is a schematic illustration of an embodiment of the invention, to which reference will be made in the description below.

Referring to FIG. 1 of the drawings, the numeral 2 designates a sheet of metal alloy (hereinafter "sheet") that is in motion during continuous production thereof. The sheet 2 to which the invention is applied is an alloy having a nominal composition that may be characterized in binary fashion, but that may show slight variations from a known, target composition, (the known, target composition being herein referred to as a "reference alloy"), wherein the primary metal has a lower atomic number, but a higher composition percentage, than the secondary metal. For example, the reference alloy may be 90 percent aluminum with trace elements (primary metal), and 10 percent zinc (secondary metal). However, at a given region along the sheet 2, a composition of, for example, 89 percent aluminum with trace elements and 11 percent zinc may obtain. Alternatively, the trace elements may be grouped with the secondary metal, the choice generally depending on whether the trace elements are collectively more similar in atomic number to the primary or the secondary metal.

A thickness measurement system in accordance with this invention includes a radiation source 6, a reference detector 8, a first detecting means 10, a second detecting means 12, and signal processing means 24. The radiation source 6 is preferably an X-ray tube. Alternatively, a radioactive source may be used. Although ionization chamber detectors are preferred, the reference detector 8, and the first and second detecting means 10, 12 may be any conventional means for detecting X-radiation, such as a scintillation counter, a Geiger-Mueller counter, or a solid state detector.

Typically, the first detecting means 10 is mounted in a first sensor housing (a portion of which is indicated as 13) which is separated from a second sensor housing (a portion of which is indicated as 15) by a pass gap 4 through which the sheet 2 travels. The source 6, reference detector 8, and second detecting means 12 are mounted in the second sensor housing 15. The sensor housings 13, 15 typically move back and forth along an axis that is perpendicular to the direction of motion of the sheet 2, thereby enabling measurement across the entire cross-machine width of the sheet. This movement is accomplished by means of a conventional sheet-traversing mechanism (not shown).

The radiation source 6 emits X-rays that are directed toward the sheet 2, as indicated. The reference detector 8 is positioned between the radiation source 6 and the sheet 2 to detect the emitted X-rays 7. In response to the detected X-rays, the reference detector 8 produces a reference signal 14 expressive of the intensity of X-rays emitted from the radiation source 6. The sheet 2 is irradiated by the X-rays, and a portion of the X-rays is transmitted through the sheet, as indicated at 16, and is detected by the first detecting means 10. In response, the first detecting means 10 produces a transmission signal 18 expressive of the intensity of transmitted X-rays 16.

The second detecting means 12 is positioned on the same side of the sheet 2 as the radiation source 6. X-rays scattered by the sheet 2 in the direction of the second detecting means 12 are indicated as 20 and are detected by the second detecting means. In response, the second detecting means 12 produces a scattering signal 22 expressive of the intensity of scattered X-rays 20.

The transmission signal 18, reference signal 14, and scattering signal 22 are inputs to signal processing means 24. The signal processing means 24 performs the mathematical operations hereinafter described. Typically, the reference, transmission, and scattering signals 14, 18, 22 require suitable amplification and filtering prior to performance of these operations. The output of the signal processing means 24 is a thickness response 26 expressive of the thickness of the sheet 2, and substantially independent of variations in composition of the sheet. The thickness responses 26 may be delivered through an appropriate interface (not shown) to a process control unit 30 typically located upstream of the thickness measurement system. Preferably, the signal processing means 24 includes a digital computer. Accordingly, it will be recognized that appropriate interfacing (not shown) should be included between those operations performed external to, and those performed by, the computer. In the preferred embodiment, all operations schematically illustrated within the signal processing means 24 of FIG. 1 are performed by a digital computer.

The transmission signal 18 and the scattering signal 22 are digitized and delivered to a first ratio analyzer 32 and second ratio analyzer 34, respectively. The reference signal 14 is digitized and delivered to both the first and second ratio analyzers 32, 34.

The first ratio analyzer 32 forms the ratio of the transmission signal 18 to the reference signal 14 and multiplies by a first calibration constant ($C_1$) that is stored in the computer memory upon performance of the calibration process hereinafter described. The resulting product is the transmittance of the sheet 2 which is expressed as a first ratio response 36. The first ratio response 36 is communicated to a first basis weight operation 38 and to a scattering reference operation 40.

The first basis weight operation 38 performs the following computation:

$$BW_1 = \frac{-\ln(R_1)}{m} ; \quad (3)$$

where "$BW_1$" is the basis weight for the reference alloy when a sample of said alloy has a transmittance equal to the observed first ratio response 36, "$R_1$" is the magnitude of the first ratio response, and "$m$" is a polynomial function of $R_1$ determined during calibration. The output of the first basis weight operation 38 is a first basis weight response 42 expressive of $BW_1$.

The scattering-reference operation 40 performs the following computation:

$$R_c = (1 - R_1^2)q \quad (4)$$

where "$q$" is a polynomial function of $R_1$ determined during calibration and "$R_c$" is the magnitude of a "predicted" second ratio response (as at 44) that should be observed, given the magnitude of $R_1$, if the composition of the sheet 2 is that of the reference alloy. The output of the scattering reference operation 40 is a comparison response 46 expressive of $R_c$.

The second ratio analyzer 34 forms the ratio of the scattering signal 22 to the reference signal 14 and multiplies by a second calibration constant ($C_2$) that is stored in the computer memory upon performance of the calibration process. The resulting product is expressed as a second ratio response 44.

The second ratio response 44 and the comparison response 46 are communicated to a composition-change operation 48 that performs the following computation:

$$P = 1 - \frac{R_2}{R_c} ; \quad (5)$$

where "$R_2$" is the magnitude of the second ratio response 44 and "$P$" indicates the degree to which the composition of the sheet differs from the reference alloy. The output of the composition-change operation 48 is a deviation response 50 expressive of P.

The deviation response 50 is communicated to a second basis weight operation 52 and a density operation 54. Also communicated to the second basis weight operation 52 is the first basis weight response 42.

The second basis weight operation 52 performs the following computation:

$$BW_c = BW_1(1 - (r-1)P) \quad (6)$$

where "$r$" is the ratio of the mass attenuation coefficient of the secondary metal to that of the primary metal, these being stored in the computer memory and communicated to the second basis weight operation as indicated at 56, and "$BW_c$" is the basis weight of the sheet 2, corrected for the deviation in composition of the sheet from the reference alloy. The output of the second basis weight operation 52 is a second basis weight response 58 expressive of $BW_c$.

The density operation 54 performs the following computation:

$$d_c = \frac{1}{\frac{(1-P)}{d_1} + \frac{P}{d_2}} ; \quad (7)$$

where "$d_1$" is the density of the reference alloy and "$d_2$" is the density of the secondary metal, these being stored in the computer memory and communicated to the density operation 54 as indicated at 60, and "$d_c$" is the density of the sheet 2, corrected for the deviation in composition of the sheet from the reference alloy. The output of the density operation 54 is a density response 62 expressive of $d_c$.

The density response 62 and the second basis weight response 58 are communicated to a thickness operation 64 wherein the ratio of $BW_c/d_c$ is formed to produce a measurement of thickness of the sheet 2. The output of the thickness operation 64, and of the signal processing means 24, is the thickness response 26. It will be recognized from the foregoing that the magnitude of the thickness response 26 will depend on the relationship between the second ratio response 44 and the comparison response 46.

As mentioned above, values for the first and second calibration constants ($C_1$, $C_2$), and for the polynomial functions "m" and "q", are determined during calibration. This calibration data is stored upon calibration in memory locations indicated as 17, 19, 21, and 23, respectively. During the measurement mode, the calibration data is recalled for use in the first and second ratio analyzers 32, 34, the first basis weight operation 38, and the scattering-reference operation 40, as indicated. During calibration, the second ratio responses 44 are communicated to the scattering-reference operation 40 (as indicated by the dashed line 45) for determination of the polynomial function "q", as is further described below.

The magnitude of the first calibration constant ($C_1$) is determined by taking the ratio of the reference signal 14 to the transmission signal 18 in the absence of the sheet 2.

The magnitude of the second calibration constant ($C_2$) is determined by positioning a sample in the pass gap 4 in place of the sheet 2, which sample has the composition of the reference alloy and a thickness that can be considered as infinite in accordance with a desired measurement accuracy, and taking the ratio of the reference signal 14 to the scattering signal 22. For example, if measurement accuracy to within a value of 0.001 for the second ratio response 44 is acceptable, then equation 1 can be used to compute the minimum thickness of the sample by substituting that value for the ratio $I/I_o$.

In order to determine values for the functions "m" and "q", a number of samples having the composition of the reference alloy, and having different thicknesses that extend over the range of thickness to be measured, are alternately positioned in the pass gap 4 in place of the sheet 2 in order to obtain a corresponding number of values for the first and second ratio responses 36, 44. As stated above, the functions "m" and "q" are polynomials and have the following form:

$$m \text{ (or } q) = K_o + K_1 \ln(R_1) + K_2 \ln^2(R_1) + \ldots + K_n \ln^n(R_1).$$

For "m", the K-values are computed to satisfy equation 3 where, in the case of the samples, "BW" values are known inputs to the computer memory.

For "q", the K-values are computed to satisfy the following function:

$$R_2 = q(1 - R_1) \qquad (8)$$

which is similar to equation 4.

What is claimed is:

1. An apparatus for measuring the thickness of a sheet of metal alloy, which apparatus is calibrated with samples of a reference alloy and which sheet has a composition that may vary from the reference alloy, comprising:
   (a) a source of X-rays positioned on one side of the sheet;
   (b) a reference detector positioned between the source and the sheet to detect X-rays emitted from the source and produce a reference signal expressive of the intensity of X-rays emitted from the source;
   (c) first detecting means positioned on the opposite side of the sheet to detect X-rays transmitted therethrough and produce a transmission signal expressive of the intensity of said transmitted radiation;
   (d) second detecting means positioned on the one side of the sheet to detect X-rays emitted from the source and scattered by the sheet and produce a scattering signal expressive of the intensity of said scattered X-rays; and
   (e) signal processing means comprising:
   means for producing a first ratio response from the transmission and reference signals, means for producing a second ratio response from the scattering and reference signals, means for producing a comparison response from the first ratio response and calibration data, and means for producing a thickness response that is expressive of the thickness of the sheet and is substantially independent of variations in composition of the sheet from the reference alloy, wherein the first ratio response is expressive of the transmittance of the sheet, the comparison response indicates what the second ratio response should be if there is no variation in composition of the sheet from the reference alloy, and the magnitude of the thickness response depends upon the degree to which the second ratio response differs from the comparison response.

2. An apparatus as in claim 1 wherein the signal processing means comprises means for computing a basis weight of the sheet, as corrected for variation in composition of the sheet from the reference alloy.

3. An apparatus as in claim 2 wherein the signal processing means comprises means for computing a density of the sheet, as corrected for variation in composition of the sheet from the reference alloy.

4. An apparatus as in claim 3 wherein the signal processing means comprises means for computing the thickness of the sheet by dividing the basis weight, as corrected for variation in composition of the sheet from the reference alloy, by the density, as corrected for variation in composition of the sheet from the reference alloy.

5. A method for measuring the thickness of a sheet of metal alloy, which sheet has a composition that may vary from a reference alloy, comprising the steps of:
   (a) detecting X-rays emitted from a source thereof to produce a reference signal expressive of the intensity of the emitted X-rays;
   (b) irradiating the sheet with the emitted X-rays;
   (c) detecting X-rays transmitted through the sheet to produce a transmission signal expressive of the intensity of transmitted X-rays;
   (d) detecting X-rays scattered from the sheet to produce a scattering signal expressive of the intensity of scattered X-rays; and
   (e) processing the reference, transmission, and scattering signals to produce a thickness response that is expressive of the thickness of the sheet and is substantially independent of variations in composition of the sheet from the reference alloy, wherein the transmission and reference signals are combined to produce a first ratio response expressive of the transmittance of the sheet, the scattering and reference signals are combined to produce a second ratio response, the first ratio response is combined with calibration data to produce a comparison response that indicates what the second ratio response should be if there is no variation in composition of the sheet from the reference alloy, and the magnitude of the thickness response depends upon the degree to which the second ratio response differs from the comparison response.

6. A method as in claim 5 wherein the processing step comprises computing a corrected basis weight of the sheet, the magnitude of which depends upon the degree to which the second ratio response differs from the comparison response.

7. A method as in claim 4 wherein the processing step further comprises computing a corrected density of the sheet, the magnitude of which depends upon the degree to which the second ratio response differs from the comparison response.

8. A method as in claim 7 wherein the magnitude of the thickness response is determined by dividing the corrected basis weight by the corrected density.

9. An apparatus for measuring the thickness of a sheet of metal alloy, which apparatus is calibrated with samples of a reference alloy, and which sheet has a composition that may vary from the reference alloy, comprising:

means positioned on one side of the sheet for irradiating the sheet with X-rays;

means positioned on the one side of the sheet for detecting X-rays that are emitted by the irradiating means to produce a reference signal expressive of the intensity of emitted X-rays;

means positioned on the opposite side of the sheet for detecting X-rays that are transmitted through the sheet to produce a transmission signal expressive of the intensity of transmitted X-rays;

means positioned on the one side of the sheet for detecting X-rays that are backscattered by the sheet to produce a scattering signal expressive of the intensity of backscattered X-rays;

signal processing means, responsive to the reference, transmission, and scattering signals, with means for producing a thickness response expressive of the thickness of the sheet, the magnitude of which thickness response depends upon the degree to which a ratio response differs from a comparison response, wherein the signal processing means comprises means to produce the ratio response in response to the reference and scattering signals, and means to produce the comparison response in response to the reference and transmission signals, and wherein the comparison response indicates what the ratio response should be if the composition of the sheet is equal to the reference alloy.

* * * * *